(12) United States Patent
Olayiwola et al.

(10) Patent No.: US 11,306,044 B2
(45) Date of Patent: *Apr. 19, 2022

(54) REMOVING OXYGEN FROM ODH PROCESS BY INJECTING ALCOHOL

(71) Applicant: NOVA Chemicals (International) S.A., Fribourg (CH)

(72) Inventors: Bolaji Olayiwola, Calgary (CA); Vasily Simanzhenkov, Calgary (CA); Shahin Goodarznia, Calgary (CA); Mohamed Aiffa, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/316,556

(22) Filed: May 10, 2021

(65) Prior Publication Data

US 2021/0309592 A1 Oct. 7, 2021

Related U.S. Application Data

(63) Continuation of application No. 16/654,680, filed on Oct. 16, 2019, now Pat. No. 11,053,179.

(30) Foreign Application Priority Data

Oct. 19, 2018 (CA) .................. CA 3021259

(51) Int. Cl.
*C07C 5/48* (2006.01)
*B01J 23/00* (2006.01)
(Continued)

(52) U.S. Cl.
CPC .............. *C07C 5/48* (2013.01); *B01J 23/002* (2013.01); *B01J 23/28* (2013.01); *B01J 23/6482* (2013.01); *B01J 23/6484* (2013.01); *B01J 23/755* (2013.01)

(58) Field of Classification Search
CPC ... C07C 5/48; C07C 7/14891; C07C 2523/20; C07C 2523/22; C07C 2523/28;
(Continued)

(56) References Cited

U.S. PATENT DOCUMENTS 5,321,192 A * 6/1994 Cottrell .................. C07C 5/321
585/659
7,687,676 B1 3/2010 Vogel et al.
(Continued)

FOREIGN PATENT DOCUMENTS

WO WO2017144584 8/2017
WO WO2018024650 2/2018

OTHER PUBLICATIONS

Kaddouri et al., "Oxidative dehydrogenation of ethane on the α and β phases of NiMoO4," Catalysis Today, Elsevier, dated Apr. 17, 1998, 40(23): 201-206.

(Continued)

*Primary Examiner* — Youngsul Jeong
*Assistant Examiner* — Jason Y Chong
(74) *Attorney, Agent, or Firm* — Fish & Richardson P.C.

(57) ABSTRACT

Provided in this disclosure is a process for the oxidative dehydrogenation of a lower alkane into a corresponding alkene. The process includes providing a gas stream comprising the lower alkane to a reactor; contacting, in the oxidative dehydrogenation reactor, the lower alkane with a catalyst that includes a mixed metal oxide; and providing to the last 50% of the oxidative dehydrogenation reactor a stream comprising from 0.01 vol. % to 10 vol. % of a $C_1$-$C_3$ alcohol.

13 Claims, 2 Drawing Sheets

(51) Int. Cl.
  *B01J 23/28* (2006.01)
  *B01J 23/648* (2006.01)
  *B01J 23/755* (2006.01)

(58) Field of Classification Search
  CPC ... C07C 2527/057; B01J 23/002; B01J 23/28; B01J 23/6482; B01J 23/6484; B01J 23/755; Y02P 20/52
  See application file for complete search history.

(56) References Cited

U.S. PATENT DOCUMENTS

| | | |
|---|---|---|
| 7,906,699 B2 | 3/2011 | Benderly et al. |
| 9,352,306 B2 * | 5/2016 | Rezai .................. B01J 29/7407 |
| 10,322,985 B1 | 6/2019 | Lin et al. |
| 11,053,179 B2 | 7/2021 | Olayiwola et al. |
| 2010/0256432 A1 * | 10/2010 | Arnold ..................... C07C 5/48 585/655 |
| 2014/0249339 A1 * | 9/2014 | Simanzhenkov ...... B01J 23/002 585/252 |
| 2020/0123085 A1 | 4/2020 | Olayiwola et al. |

OTHER PUBLICATIONS

International Search Report and Written Opinion in International Application No. PCT/IB2019/058866, dated Jan. 8, 2020, 10 pages.

* cited by examiner

Simplified Reactor Diagram

REMOVING OXYGEN FROM ODH PROCESS BY INJECTING ALCOHOL

CROSS REFERENCE TO RELATED APPLICATIONS

This application is a continuation of and claims the benefit of priority to U.S. patent application Ser. No. 16/654,680, filed on Oct. 16, 2019, which claims the benefit of the earlier filing date of Canadian application serial number 3,021,259 filed on Oct. 19, 2018, the contents of which are hereby incorporated by reference.

TECHNICAL FIELD

The present disclosure relates generally to oxidative dehydrogenation (ODH) of lower alkanes (e.g., $C_2H_6$ through $C_8H_{18}$ alkanes) into corresponding alkenes. More specifically, the present disclosure relates to an ODH process that includes multiple reactors in series.

BACKGROUND

Catalytic oxidative dehydrogenation of alkanes into corresponding alkenes is an alternative to steam cracking; steam cracking is the method of choice for the majority of today's commercial-scale producers. Despite its widespread use, steam cracking has its downsides. Steam cracking is energy intensive, requiring temperatures in the range of 700° C. to 1,000° C. to satisfy the highly endothermic nature of the cracking reactions. This also results in significant amounts of greenhouse gasses. The process is expensive owing to the high fuel demand, the requirement for reactor materials that can withstand the high temperatures, and the necessity for separation of unwanted by-products using downstream separation units. The production of coke by-product requires periodic shutdown for cleaning and maintenance. For ethylene producers, the selectivity for ethylene is only around 80-85% for a conversion rate that does not generally exceed 60%. In contrast, ODH operates at lower temperatures, produces insignificant amounts of greenhouse gasses, does not produce coke, and using newer-developed catalysts provides selectivity for ethylene of around 98% at close to 60% conversion.

It is beneficial to operate an ODH reactor with at least a small amount of oxygen remaining in the reactor product stream. This is done to preserve the ODH catalyst from permanent damage or deactivation which is caused by exposing it to an oxygen-free reducing environment at elevated temperature.

Another reason to operate with at least a small amount of oxygen is to ensure that all of the ODH catalyst bed is being utilized instead of only the first portion of the reactor, which can occur when the ODH product stream is less than 1 ppm $O_2$. However, oxygen being present in the ODH product gas stream can cause operational issues in the downstream equipment, primarily at—and downstream of—the first compression stage of the ODH plant. As a result, there is a need to remove oxygen to a very low to non-detectable levels before the product gas compression.

SUMMARY

Provided in this disclosure is a process for the oxidative dehydrogenation of a lower alkane into a corresponding alkene. The process includes providing a gas stream comprising the lower alkane to a reactor; contacting, in the oxidative dehydrogenation reactor, the lower alkane with a catalyst that includes a mixed metal oxide; and providing to the last 50% of the oxidative dehydrogenation reactor a stream comprising from 0.01 vol. % to 20 vol. % of a $C_1$-$C_3$ alcohol.

In some embodiments, the stream including the $C_1$-$C_3$ alcohol includes 15 vol. % of a $C_1$-$C_3$ alcohol. In some embodiments, the stream including the $C_1$-$C_3$ alcohol includes 13.6 vol. % of a $C_1$-$C_3$ alcohol. In some embodiments, the stream including the $C_1$-$C_3$ alcohol includes 10 vol. % of a $C_1$-$C_3$ alcohol.

In some embodiments, the stream that includes the $C_1$-$C_3$ alcohol further includes an inert gas.

In some embodiments, the effluent includes less than 100 parts per million by volume (ppmv) $O_2$.

In some embodiments, the stream that includes the $C_1$-$C_3$ alcohol is provided to the last 30% of the oxidative dehydrogenation reactor. For example, the stream that includes the $C_1$-$C_3$ alcohol can be provided to the last 10% of the oxidative dehydrogenation reactor.

In some embodiments, the oxidative dehydrogenation catalyst includes a mixed metal oxide selected from the group consisting of: (i) a catalyst of the formula:

$$Mo_aV_bTe_cNb_dPd_eO_f$$

wherein a is 1, b is from 0.01 to 1.0, c is from 0.01 to 1.0, d is from 0.01 to 1.0, e is from 0.00 to 0.10, and f is a number to satisfy the valence state of the catalyst; (ii) a catalyst of the formula:

$$Ni_gA_hB_iD_jO_f$$

wherein: A is selected from the group consisting of Ti, Ta, V, Nb, Hf, W, Y, Zn, Zr, Si and Al or mixtures thereof; B is selected from the group consisting of La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, or a mixture thereof; D is selected from the group consisting of Ca, K, Mg, Li, Na, Sr, Ba, Cs, and Rb or a mixture thereof; and O is oxygen; and g is from 0.1 to 0.9, h is from 0.04 to 0.9; i is from 0 to 0.5; j is from 0 to 0.5; and f is a number to satisfy the valence state of the catalyst; (iii) a catalyst of the formula:

$$Mo_aE_kG_lO_f$$

wherein: E is selected from the group consisting of Ba, Ca, Cr, Mn, Nb, Ta, Ti, Te, V, W or a mixture thereof; G is selected from the group consisting of Bi, Ce, Co, Cu, Fe, K, Mg, V, Ni, P, Pb, Sb, Si, Sn, Ti, U, or a mixture thereof; a is 1; k is from 0 to 2; l is from 0 to 2, with the proviso that the total value of I for Co, Ni, Fe or a mixture thereof is less than 0.5; and f is a number to satisfy the valence state of the catalyst; (iv) a catalyst of the formula:

$$V_mMo_nNb_pTe_qMe_rO_f$$

wherein: Me is a metal selected from the group consisting of Ta, Ti, W, Hf, Zr, Sb or a mixture thereof; m is from 0.1 to 3; n is from 0.5 to 1.5; p is from 0.001 to 3; q is from 0.001 to 5; r is from 0 to 2; and f is a number to satisfy the valence state of the catalyst; and (v) a catalyst of the formula:

$$Mo_aV_rX_sY_tZ_uM_vO_f$$

wherein: X is Nb, Ta, or a mixture thereof; Y is Sb, Ni, or a mixture thereof; Z is Te, Ga, Pd, W, Bi, Al, or a mixture thereof; M is Fe, Co, Cu, Cr, Ti, Ce, Zr, Mn, Pb, Mg, Sn, Pt, Si, La, K, Ag, In, or a mixture thereof; a is 1; r is from 0.05 to 1.0; s is from 0.001 to 1.0; t is from 0.001 to 1.0; u is from 0.001 to 0.5; v is from 0.001 to 0.3; and f is a number to satisfy the valence state of the catalyst.

In some embodiments, the lower alkane is a $C_1$-$C_3$ alkane. For example, the lower alkane can be ethane.

In some embodiments, the $C_1$-$C_3$ alcohol includes ethanol.

In some embodiments, the effluent includes a carboxylic acid. For example, the effluent can include acetic acid.

In some embodiments, the process includes two or more oxidative dehydrogenation reactors. In some embodiments, at least one of the oxidative dehydrogenation reactors is a fixed bed type reactor. In some embodiments, at least one of the oxidative dehydrogenation reactors is a single fluidized bed type reactor. In some embodiments, at least one of the oxidative dehydrogenation reactors is a moving bed type reactor. In some embodiments, at least one of the oxidative dehydrogenation reactors is an ebulliated bed type reactor. In some embodiments, at least one of the oxidative dehydrogenation reactors is a shell and tube reactor. In some embodiments, at least one of the oxidative dehydrogenation reactors is a tube reactor.

In some embodiments, the $C_1$-$C_3$ alcohol is at a concentration of 0.05 vol. % to 2 vol. %.

In some embodiments, the $C_1$-$C_3$ alcohol stream is provided at a temperature above the dew point of the effluent stream.

In some embodiments, the $C_1$-$C_3$ alcohol stream is provided at a temperature from 140° C. to 380° C. In some embodiments, the $C_1$-$C_3$ alcohol stream is provided at a temperature from 140° C. to 200° C.

Also provided in this disclosure is a process for the oxidative dehydrogenation of a lower alkane to a corresponding alkene that includes providing a stream that includes from 0.01 vol. % to 20 vol. % of a $C_1$-$C_3$ alcohol to an effluent of one or more oxidative dehydrogenation reactors upstream of a downstream oxidative dehydrogenation reactor to provide an $O_2$ consuming stream; and providing the $O_2$ consuming stream to the downstream oxidative dehydrogenation reactor.

In some embodiments, the stream including the $C_1$-$C_3$ alcohol includes 15 vol. % of a $C_1$-$C_3$ alcohol. In some embodiments, the stream including the $C_1$-$C_3$ alcohol includes 13.6 vol. % of a $C_1$-$C_3$ alcohol. In some embodiments, the stream including the $C_1$-$C_3$ alcohol includes 10 vol. % of a $C_1$-$C_3$ alcohol.

In some embodiments, the effluent of the downstream oxidative dehydrogenation reaction includes less than 100 ppmv $O_2$.

In some embodiments, the stream including the $C_1$-$C_3$ alcohol further includes an inert gas.

In some embodiments, the process includes contacting, in one or more of the oxidative dehydrogenation reactors, the lower alkane with a catalyst comprising a mixed metal oxide.

In some embodiments, the catalyst including the mixed metal oxide is selected from the group consisting of: (i) a catalyst of the formula:

$$Mo_aV_bTe_cNb_dPd_eO_f$$

wherein a is 1, b is from 0.01 to 1.0, c is from 0.01 to 1.0, d is from 0.01 to 1.0, e is from 0.00 to 0.10, and f is a number to satisfy the valence state of the catalyst; (ii) a catalyst of the formula:

$$Ni_gA_hB_iD_jO_f$$

wherein A is selected from the group consisting of Ti, Ta, V, Nb, Hf, W, Y, Zn, Zr, Si and Al or mixtures thereof; B is selected from the group consisting of La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, or a mixture thereof; D is selected from the group consisting of Ca, K, Mg, Li, Na, Sr, Ba, Cs, and Rb or a mixture thereof; and O is oxygen; and g is from 0.1 to 0.9, h is from 0.04 to 0.9; i is from 0 to 0.5; j is from 0 to 0.5; and f is a number to satisfy the valence state of the catalyst; (iii) a catalyst of the formula:

$$Mo_aE_kG_lO_f$$

wherein E is selected from the group consisting of Ba, Ca, Cr, Mn, Nb, Ta, Ti, Te, V, W or a mixture thereof; G is selected from the group consisting of Bi, Ce, Co, Cu, Fe, K, Mg, V, Ni, P, Pb, Sb, Si, Sn, Ti, U, or a mixture thereof; a is 1; k is from 0 to 2; l is from 0 to 2, with the proviso that the total value of l for Co, Ni, Fe or a mixture thereof is less than 0.5; and f is a number to satisfy the valence state of the catalyst; (iv) a catalyst of the formula:

$$V_mMo_nNb_pTe_qMe_rO_f$$

wherein Me is a metal selected from the group consisting of Ta, Ti, W, Hf, Zr, Sb or a mixture thereof; m is from 0.1 to 3; n is from 0.5 to 1.5; p is from 0.001 to 3; q is from 0.001 to 5; r is from 0 to 2; and f is a number to satisfy the valence state of the catalyst; and (v) a catalyst of the formula:

$$Mo_aV_rX_sY_tZ_uM_vO_f$$

wherein X is Nb, Ta, or a mixture thereof; Y is Sb, Ni or a mixture thereof; Z is Te, Ga, Pd, W, Bi, Al, or a mixture thereof; M is Fe, Co, Cu, Cr, Ti, Ce, Zr, Mn, Pb, Mg, Sn, Pt, Si, La, K, Ag, In, or a mixture thereof; a is 1; r is from 0.05 to 1.0; s is from 0.001 to 1.0; t is from 0.001 to 1.0; u is from 0.001 to 0.5; v is from 0.001 to 0.3; and f is a number to satisfy the valence state of the catalyst.

In some embodiments, the lower alkane is a $C_1$-$C_3$ alkane. For example, the lower alkane can be ethane.

In some embodiments, the $C_1$-$C_3$ alcohol includes ethanol.

In some embodiments, the effluent of the downstream oxidative dehydrogenation reaction includes a carboxylic acid. For example, the effluent of the downstream oxidative dehydrogenation reaction can include acetic acid.

In some embodiments, at least one of the oxidative dehydrogenation reactors is a fixed bed type reactor. In some embodiments, at least one of the oxidative dehydrogenation reactors is a single fluidized bed type reactor. In some embodiments, at least one of the oxidative dehydrogenation reactors is a moving bed type reactor. In some embodiments, at least one of the oxidative dehydrogenation reactors is an ebulliated bed type reactor. In some embodiments, at least one of the oxidative dehydrogenation reactors is a shell and tube reactor. In some embodiments, at least one of the oxidative dehydrogenation reactors is a tube reactor.

In some embodiments, the $C_1$-$C_3$ alcohol is at a concentration of 0.05 vol. % to 2 vol. % in the stream provided to the effluent of the one or more oxidative dehydrogenation reactors upstream of the downstream oxidative dehydrogenation reactor.

In some embodiments, the $C_1$-$C_3$ alcohol stream is provided at a temperature above the dew point of the effluent stream.

In some embodiments, the $C_1$-$C_3$ alcohol stream is provided at a temperature of from 140° C. and 380° C.

In some embodiments, the $C_1$-$C_3$ alcohol stream is provided at a temperature of from 140° C. and 200° C.

DETAILED DESCRIPTION

Figure 1:
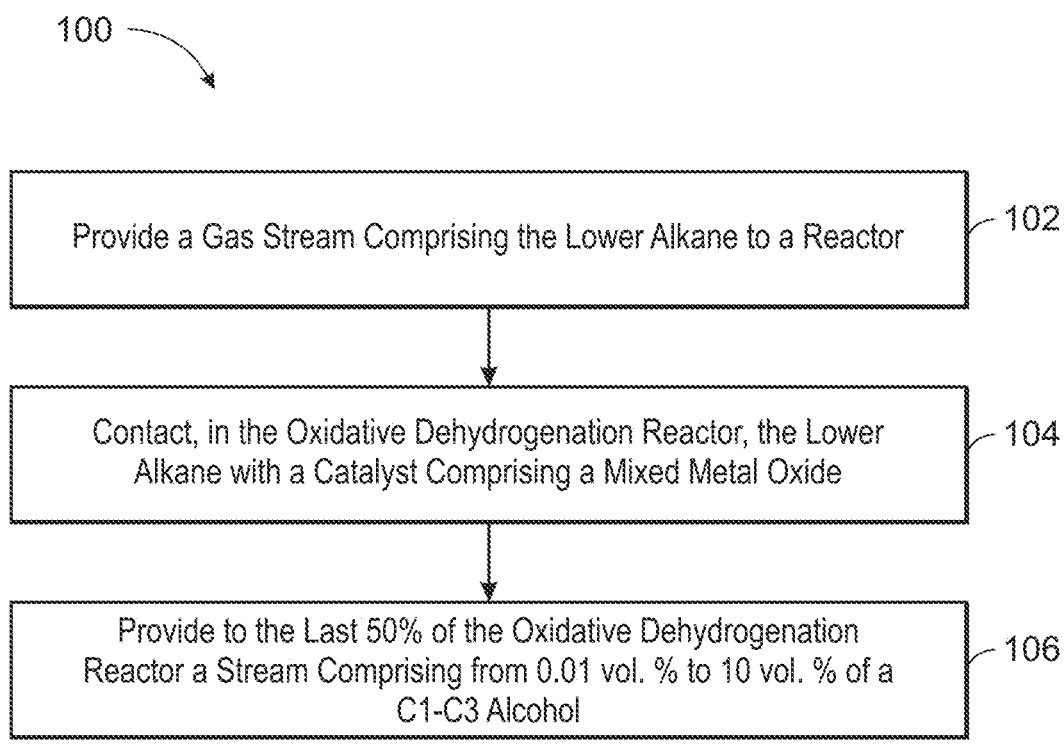
FIG. 1 shows a flowchart of an example method of a process for the oxidative dehydrogenation of a lower alkane into a corresponding alkene.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present invention desires to obtain. At the very least, and not as an attempt to limit the application of the doctrine of equivalents to the scope of the claims, each numerical parameter should at least be construed in light of the number of reported significant digits and by applying ordinary rounding techniques.

As used herein, the term "inert gas" is defined as a gas with no or low reactivity to an oxidative dehydrogenation catalyst. These gases include nitrogen, steam, carbon dioxide, argon, or mixtures thereof.

As used herein, the term "dilute air" is defined as a gas which contains air, and also inert gas such that the concentration of oxygen is less than about 8% by volume.

As used herein, the term "fixed bed reactor" is defined as any closed body, typically cylindrical or spherical, having inlets and outlets, filled with catalyst pellets with reactants flowing through the bed and being converted into products. The catalyst may have multiple configuration including: one large bed, several horizontal beds, several parallel packed tubes, multiple beds in their own shells. The various configurations may be adapted depending on the need to maintain temperature control within the system. The pellets may be spherical, cylindrical, or randomly shaped pellets. As used herein, a "fixed bed reactor unit" can consist of one, two or more fixed bed tubular reactors in series.

In the following description of the present disclosure, for reference to the figure it should be noted that like parts are designated by like reference numbers.

The ODH of lower alkanes includes contacting a mixture of a lower alkane and oxygen in an ODH reactor with an ODH catalyst under conditions that promote oxidation of the lower alkane into its corresponding alkene. Conditions within the reactor are controlled by the operator and include, but are not limited to, parameters such as temperature, pressure, and flow rate. Conditions will vary and can be optimized for a particular lower alkane, or for a specific catalyst, or whether an inert diluent is used in the mixing of the reactants.

Use of an ODH reactor for performing an ODH process consistent with the present invention falls within the knowledge of the person skilled in the art. For best results, the oxidative dehydrogenation of a lower alkane may be conducted at temperatures from 300° C. to 450° C., typically from 300° C. to 425° C., such as from 330° C. to 400° C., at pressures from 0.5 to 100 psi (3.447 to 689.47 kPa), such as from 15 to 50 psi (103.4 to 344.73 kPa), and the residence time of the lower alkane in the reactor is typically from 0.002 to 30 seconds, such as from 1 to 10 seconds.

The process can have a selectivity for the corresponding alkene (ethylene in the case of ethane ODH) of greater than 85%, such as, greater than 90%. The flow of reactants and inert diluent can be described in any number of ways known in the art. Typically, flow is described and measured in relation to the volume of all feed gases (reactants and diluent) that pass over the volume of the active catalyst bed in one hour, or gas hourly space velocity (GHSV). The GHSV can range from 500 to 30000 $h^{-1}$, such as greater than 1000 $h^{-1}$. The flow rate can also be measured as weight hourly space velocity (WHSV), which describes the flow in terms of the weight, as opposed to volume, of the gases that flow over the weight of the active catalyst per hour. In calculating WHSV the weight of the gases may include only the reactants but may also include diluents added to the gas mixture. When including the weight of diluents, when used, the WHSV may range from 0.5 $h^{-1}$ to 50 $h^{-1}$, such as from 1.0 to 25.0 $h^{-1}$.

The flow of gases through the reactor may also be described as the linear velocity of the gas stream (m/s), which is defined in the art as the flow rate of the gas stream/cross-sectional surface area of the reactor/void fraction of the catalyst bed. The flow rate generally means the total of the flow rates of all the gases entering the reactor and is measured where the oxygen and alkane first contact the catalyst and at the temperature and pressure at that point. The cross-section of the reactor is also measured at the entrance of the catalyst bed. The void fraction of the catalyst bed is defined as the volume of voids in the catalyst bed/total volume of the catalyst bed. The volume of voids refers to the voids between catalyst particles and does not include the volume of pores inside the catalyst particles. The linear velocity can range from 5 cm/sec to 1500 cm/sec, such as from 10 cm/sec to 500 cm/sec.

The space-time yield of corresponding alkene (productivity) in g/hour per kg of the catalyst should be not less than 900, such as greater than 1500, or greater than 3000, or greater than 3500 at 350° C. to 400° C. It should be noted that the productivity of the catalyst can increase with increasing temperature until the selectivity is sacrificed.

The oxidative dehydrogenation process can use an oxidative dehydrogenation catalyst comprising a mixed metal oxide selected from the group consisting of:

i) catalysts of the formula:

wherein a, b, c, d, e and f are the relative atomic amounts of the elements Mo, V, Te, Nb, Pd and O, respectively; and when a is 1, b is from 0.01 to 1.0, c is from 0.01 to 1.0, d is from 0.01 to 1.0, e is from 0 to 0.10, and f is a number to satisfy the valence state of the catalyst;

ii) catalysts of the formula:

wherein g is from 0.1 to 0.9, such as from 0.3 to 0.9, or from 0.5 to 0.85, or from 0.6 to 0.8; h is from 0.04 to 0.9; i is from 0 to 0.5; j is from 0 to 0.5; and f is a number to satisfy the valence state of the catalyst; A is selected from the group consisting of Ti, Ta, V, Nb, Hf, W, Y, Zn, Zr, Si and Al or mixtures thereof; B is selected from the group consisting of La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, or a mixture thereof; D is selected from the group consisting of Ca, K, Mg, Li, Na, Sr, Ba, Cs, and Rb or a mixture thereof; and O is oxygen;

iii) catalysts of the formula:

wherein E is selected from the group consisting of Ba, Ca, Cr, Mn, Nb, Ta, Ti, Te, V, W or a mixture thereof; G is selected from the group consisting of Bi, Ce, Co, Cu, Fe, K, Mg, V, Ni, P, Pb, Sb, Si, Sn, Ti, U, or a mixture thereof; a is 1; k is from 0 to 2; I is from 0 to 2, with the proviso that the total value of I for Co, Ni, Fe or a mixture thereof is less than 0.5; and f is a number to satisfy the valence state of the catalyst;

iv) catalysts of the formula:

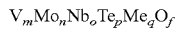
$$V_m Mo_n Nb_o Te_p Me_q O_f$$

wherein Me is a metal selected from the group consisting of Ta, Ti, W, Hf, Zr, Sb or a mixture thereof; m is from 0.1 to 3; n is from 0.5 to 1.5; o is from 0.001 to 3; p is from 0.001 to 5; q is from 0 to 2; and f is a number to satisfy the valence state of the catalyst; and v) and catalysts of the formula:

$$Mo_a V_r X_s Y_t Z_u M_v O_f$$

wherein X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a is 1; r is from 0.05 to 1.0; s is from 0.001 to 1.0; t is from 0.001 to 1.0; u is from 0.001 to 0.5; v is from 0.001 to 0.3; and f is a number to satisfy the valence state of the catalyst.

The present disclosure includes a process to remove $O_2$ from the ODH reactor, or the last ODH reactor assuming that there are multiple reactors in series, by means of adding mixture of a $C_1$-$C_3$ alcohol, such as ethanol, and steam, into this reactor to consume the residual $O_2$ by reacting it with alcohol, such as ethanol, to generate the corresponding carboxylic acid, such as acetic acid. The ODH reactor(s) can be fixed bed, fluidized bed, moving bed, ebulliated bed, shell and tube or tube reactor design. The alcohol concentration may be from 0.5 to 2 vol % of the alcohol and steam mixture. The reaction operating temperature for this bed is in the range of 150° C. up to desired ODH reaction temperature. Once the $O_2$ is fully consumed in this reactor, the remaining alcohol, such as ethanol, is catalytically dehydrated to generate an alkene, such as ethylene, in the same reactor.

FIG. 1 is a flowchart of an example method 100 of a process for the oxidative dehydrogenation of a lower alkane into a corresponding alkene. At 102, a gas stream comprising the lower alkane is provided to a reactor. At 104, the lower alkane is contacted, in the oxidative dehydrogenation reactor, with a catalyst comprising a mixed metal oxide. At 106, a stream comprising from 0.01 vol. % to 10 vol. % of a $C_1$-$C_3$ alcohol is provided to the last 50% of the oxidative dehydrogenation reactor.

It is speculative that the portion of the exothermic heat of reaction for converting ethanol to acetic acid provides heat of reaction for the endothermic reaction of ethanol dehydration to ethylene. As a result, addition of small concentration of ethanol to the last reactor generates relatively small net heat of reaction, which can enable the one tube or adiabatic fixed bed reactor design, as opposed to tube and shell heat exchanger reactor design, which can lead to capital cost savings.

Presence of ethanol and steam in the last reactor bed was found to preserve the catalyst from deactivation in the $O_2$-free environment. The benefits of the explained $O_2$ removal process are summarized as including (i) $O_2$ removal from ODH product stream to avoid fouling in the separation and compression train downstream of the ODH reactors while preserving the catalyst activity in the last reactor bed; (ii) $O_2$ removal from ODH product stream to avoid degradation of the amine system for removing $CO_2$ and $H_2S$ into heat-stable amine salts; enabling a tube reactor design, as opposed to tube and shell heat exchanger reactor design, for the last ODH reactor, which can lead to capital cost savings; increases in ethylene yield in the ODH process by converting portion of the ethanol into ethylene; and ethanol can come from multiple sources including acetic acid hydrogenation from the ODH itself, bio-sources, ethylene hydration, etc. Inclusion of even small amounts of bioethanol to scavenge trace oxygen can produce two useful commercial co-products, acetic acid and ethylene.

The present disclosure will further be described by reference to the following examples. The following examples are merely illustrative and are not intended to be limiting. Unless otherwise indicated, all percentages are by weight.

EXAMPLES

Figure 2:
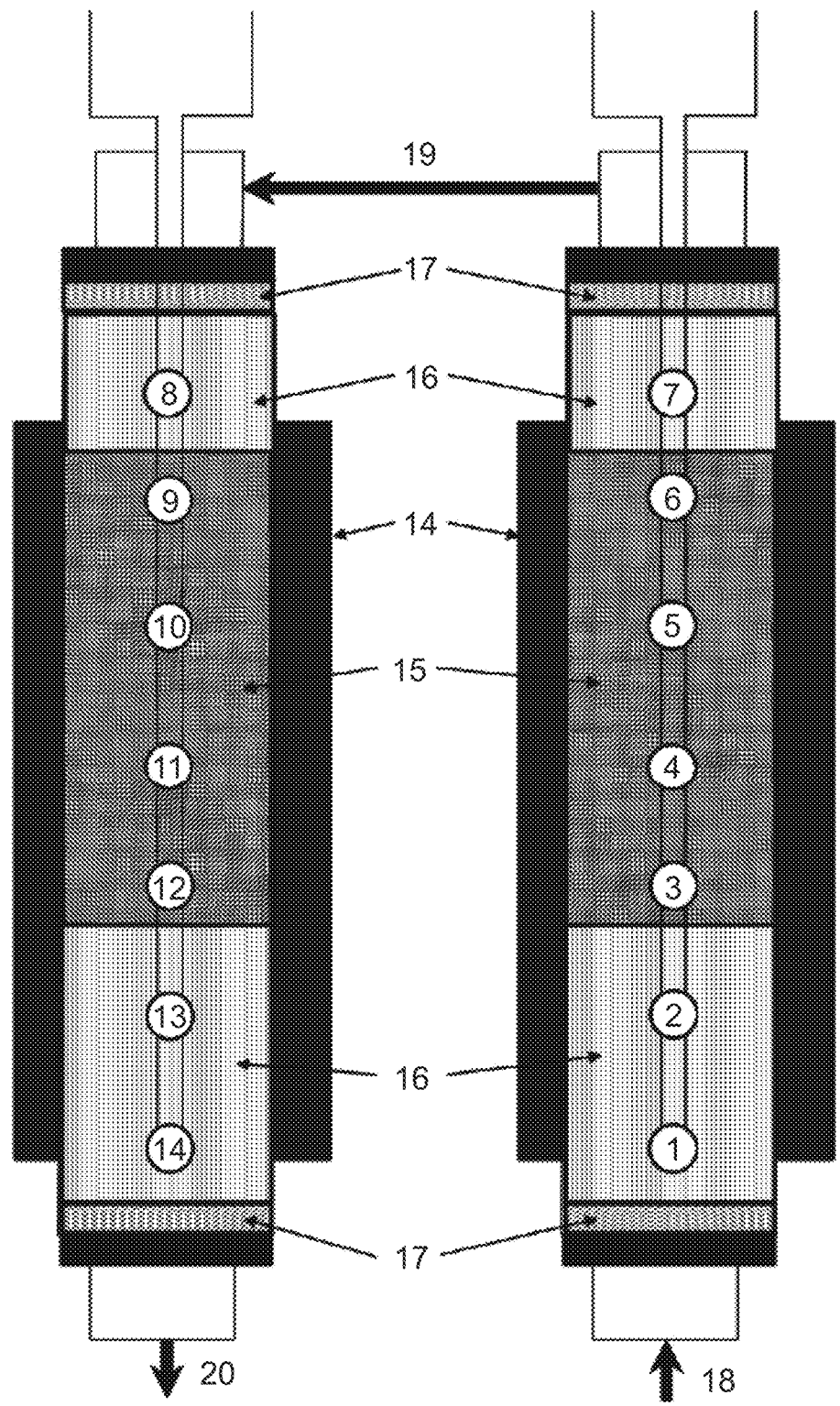
FIG. 2 shows a simplified reactor set up diagram with two fixed bed ODH reactors.

A Fixed Bed Reactor Unit (FBRU) was used to conduct experiments on residual $O_2$ removal. The apparatus is shown in FIG. 2 and consisted of two fixed bed tubular reactors in series. Each reactor was wrapped in an electrical heating jacket and sealed with ceramic insulating material. Each reactor was SS316L tube which had an outer diameter of 1" and is 34" in length. In these experiments, ethane, ethylene, carbon dioxide, oxygen, nitrogen were fed separately (on as-needed basis) and pre-mixed prior to the reactor inlet, 18, with the indicated composition (given in each experiment). The flow passed from the upstream reactor to the downstream reactor at stream 19, and the product stream exited the downstream reactor at stream 20. Both reactors were being controlled at the same reaction temperature. The temperature of each of the reactors were monitored using corresponding 7-point thermocouples shown by 1-7 in the upstream reactor, and 8-14 in the downstream reactor. The highest temperature between thermocouple points was used for controlling the reactor temperature using the corresponding back pressure regulator that controlled the pressure and boiling temperature of water inside the desired reactor water jacket, 14. It is noteworthy that only thermocouple points 3 to 6 in the upstream reactor and 9 to 12 in the downstream reactor were located in the reactor bed, and the reaction temperature for each reactor was being reported as an average of these points.

The catalyst bed, 15, consisted of one weight unit of catalyst to 2.14 units of weight of Denstone 99 (mainly alpha alumina) powder; total weight of the catalyst in each reactor was 143 g catalyst having the formula $MoV_{0.40}Nb_{0.16}Te_{0.14}O$, with relative atomic amounts of each component, relative to a relative amount of Mo of 1, shown in subscript. The rest of the reactor, below and above the catalyst bed was packed with quartz powder, 16, and secured in place with glass wool, 17, on the top and the bottom of the reactor tube to avoid any bed movement during the experimental runs.

TABLE 1

ODH Residual $O_2$ Removal Example

| | $C_2H_6$ | $C_2H_4$ | $O_2$ | $CO_2$ | $C_2H_5OH$ | $H_2O$ | $CH_3COOH$ |
|---|---|---|---|---|---|---|---|
| Feed Gas composition (dry basis, vol %) | 11.0 | 87.9 | 0.6 | 0.6 | | | |
| Feed Liquid composition (vol%) | | | | | 13.6 | 85.9 | 0.0 |
| Product Gas composition (dry basis, vol %) | 10.7 | 88.7 | 0.0 | 0.6 | | | |
| Product Liquid composition (vol %) | | | | | 2.4 | 93.3 | 4.3 |

TABLE 2

Catalyst activity converting ethanol to ethylene and
acetic acid during ODH Residual O₂ Removal Example

| | | |
|---|---|---|
| Ethanol conversion (C-atom %) | | 87 |
| Yield (wt %) | $C_2H_4$ | 59 |
| | $CH_3COOH$ | 28 |
| Selectivity (wt %) | $C_2H_4$ | 68 |
| | $CH_3COOH$ | 32 |

TABLE 3

Catalyst activity before and after
ODH Residual O₂ Removal Example

| | | Before | After |
|---|---|---|---|
| GHSV (h⁻¹) | | 825 | 825 |
| Reaction temperature (° C.) | | 321 | 321 |
| Reactor 1 inlet pressure (psig) | | 18.3 | 18.8 |
| Feed (vol %) | $C_2H_6$ | 82 | 82 |
| | $O_2$ | 18 | 18 |
| Ethane conversion (wt %) | | 13 | 13 |
| $C_2H_4$ yield (g $C_2H_4$/g cat/hr) | | 0.09 | 0.09 |
| Selectivity (wt %) | $C_2H_4$ | 91 | 91 |
| | $CO_2$ | 2 | 2 |
| | CO | 3 | 3 |
| | $CH_3COOH$ | 5 | 5 |

What is claimed is:

1. A process for the oxidative dehydrogenation of a lower alkane into a corresponding alkene, the process comprising:
providing a gas stream comprising the lower alkane and oxygen to an oxidative dehydrogenation reactor;
contacting, in the oxidative dehydrogenation reactor, the lower alkane with an oxidative dehydrogenation catalyst comprising a mixed metal oxide;
providing a stream comprising from 0.01 vol. % to 10 vol. % of a $C_1$-$C_3$ alcohol to the oxidative dehydrogenation reactor within the last 50% of the total reaction zone in the oxidative dehydrogenation reactor; and obtaining an effluent comprising the corresponding alkene.

2. The process of claim 1, wherein the stream comprising the $C_1$-$C_3$ alcohol further comprises an inert gas.

3. The process of claim 1, wherein the effluent comprises less than 100 parts per million by volume (ppmv) $O_2$.

4. The process of claim 1, wherein the stream comprising the $C_1$-$C_3$ alcohol is provided to the oxidative dehydrogenation reactor within the last 30% of the total reaction zone in the oxidative dehydrogenation reactor.

5. The process of claim 1, wherein the stream comprising the $C_1$-$C_3$ alcohol is provided to the oxidative dehydrogenation reactor within the last 10% of the total reaction zone in the oxidative dehydrogenation reactor.

6. The process of claim 1, wherein the oxidative dehydrogenation catalyst comprises a mixed metal oxide selected from the group consisting of:

(i) a catalyst of the formula:

$$Mo_aV_bTe_cNb_dPd_eO_f$$

wherein a is 1, b is from 0.01 to 1.0, c is from 0.01 to 1.0, d is from 0.01 to 1.0, e is from 0.00 to 0.10, and f is a number to satisfy the valence state of the catalyst;

(ii) a catalyst of the formula:

$$Ni_gA_hB_iD_jO_f$$

wherein:

A is selected from the group consisting of Ti, Ta, V, Nb, Hf, W, Y, Zn, Zr, Si and Al or mixtures thereof;
B is selected from the group consisting of La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, or a mixture thereof;
D is selected from the group consisting of Ca, K, Mg, Li, Na, Sr, Ba, Cs, and Rb or a mixture thereof; and
O is oxygen; and
g is from 0.1 to 0.9, h is from 0.04 to 0.9; i is from 0 to 0.5; j is from 0 to 0.5; and, f is a number to satisfy the valence state of the catalyst;

(iii) a catalyst of the formula:

$$Mo_aE_kG_lO_f$$

wherein:

E is selected from the group consisting of Ba, Ca, Cr, Mn, Nb, Ta, Ti, Te, V, W or a mixture thereof;
G is selected from the group consisting of Bi, Ce, Co, Cu, Fe, K, Mg, V, Ni, P, Pb, Sb, Si, Sn, Ti, U, or a mixture thereof;
a is 1; k is from 0 to 2; I is from 0 to 2, with the proviso that the total value of I for Co, Ni, Fe or a mixture thereof is less than 0.5; and f is a number to satisfy the valence state of the catalyst;

(iv) a catalyst of the formula:

$$V_mMo_nNb_pTe_qMe_rO_f$$

wherein:

Me is a metal selected from the group consisting of Ta, Ti, W, Hf, Zr, Sb or a mixture thereof;
m is from 0.1 to 3; n is from 0.5 to 1.5; p is from 0.001 to 3; q is from 0.001 to 5; r is from 0 to 2; and f is a number to satisfy the valence state of the catalyst; and (v) a catalyst of the formula:

$$Mo_aV_rX_sY_tZ_uM_vO_f$$

wherein:

X is Nb, Ta, or a mixture thereof; Y is Sb, Ni, or a mixture thereof;
Z is Te, Ga, Pd, W, Bi, Al, or a mixture thereof;
M is Fe, Co, Cu, Cr, Ti, Ce, Zr, Mn, Pb, Mg, Sn, Pt, Si, La, K, Ag, In, or a mixture thereof;
a is 1; r is from 0.05 to 1.0; s is from 0.001 to 1.0; t is from 0.001 to 1.0; u is from 0.001 to 0.5; v is from 0.001 to 0.3; and f is a number to satisfy the valence state of the catalyst.

7. The process of claim 1, wherein the lower alkane is a $C_1$-$C_3$ alkane.

8. The process of claim 1, wherein the lower alkane is ethane.

9. The process of claim 1, wherein the effluent comprises a carboxylicacid carboxylic acid.

10. The process of claim 1, wherein the $C_1$-$C_3$ alcohol comprises ethanol.

11. The process of claim 1, wherein the effluent comprises acetic acid.

12. The process of claim 1, wherein the process comprises two or more oxidative dehydrogenation reactors.

13. The process of claim 1, wherein the $C_1$-$C_3$ alcohol is at a concentration of 0.05 vol. % to 2 vol. %.

* * * * *

UNITED STATES PATENT AND TRADEMARK OFFICE
CERTIFICATE OF CORRECTION

PATENT NO. : 11,306,044 B2
APPLICATION NO. : 17/316556
DATED : April 19, 2022
INVENTOR(S) : Bolaji Olayiwola et al.

It is certified that error appears in the above-identified patent and that said Letters Patent is hereby corrected as shown below:

In the Claims

In Column 9, Line 63, In Claim 6, delete "NigAhBiDj Of" and insert -- NigAhBiDjOf --.

In Column 10, Line 3, In Claim 6, delete "Bis" and insert -- B is --.

In Column 10, Line 15 (Approx.), In Claim 6, delete "MOaEkGlOf" and insert -- MoaEkGlOf --.

In Column 10, Line 38 (Approx.), In Claim 6, delete "MoaVrXsYtZuMvOr" and insert
-- MoaVrXsYtZuMvOf --.

In Column 10, Line 55, In Claim 9, delete "carboxylicacid carboxylic" and insert -- carboxylic --.

Signed and Sealed this
Twenty-eighth Day of June, 2022

Katherine Kelly Vidal
*Director of the United States Patent and Trademark Office*